United States Patent [19]

Ross

[11] 3,994,967

[45] Nov. 30, 1976

[54] COLOR DEVELOPER COMPOSITIONS CONTAINING IMPROVED YELLOW DYE-FORMING COUPLER

[75] Inventor: Robert E. Ross, Rochester, N.Y.

[73] Assignee: Eastman Kodak Company, Rochester, N.Y.

[22] Filed: June 2, 1975

[21] Appl. No.: 583,340

Related U.S. Application Data

[60] Continuation-in-part of Ser. No. 449,800, March 8, 1974, abandoned, Division of Ser. No. 492,116, July 26, 1974, Pat. No. 3,929,484.

[52] U.S. Cl. .......................... 260/519; 260/471 R; 260/471 H

[51] Int. Cl.[2] .......................... C07C 101/72

[58] Field of Search ............ 260/519, 471 R, 471 A

[56] References Cited

UNITED STATES PATENTS

| | | | |
|---|---|---|---|
| 3,277,155 | 10/1966 | Loria et al. | 260/519 X |
| 3,384,657 | 5/1968 | Weissberger et al. | 260/591 X |
| 3,408,194 | 10/1968 | Loria | 96/100 |
| 3,644,498 | 2/1972 | Loria | 260/519 x |

*Primary Examiner*—Helen M. S. Sneed
*Attorney, Agent, or Firm*—J. G. Levitt

[57] ABSTRACT

Color developer compositions are described which contain, dissolved therein, both (a) an organic aromatic primary amino developing agent and (b) a yellow-dye-forming coupler having the structure:

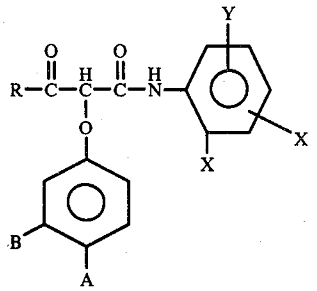

wherein R is a branched alkyl group containing 3 to 6 carbon atoms; X is Cl or Br; Y is X, hydrogen or alkyl (1 to 8 carbon atoms); and A and B differ and are either H or —COOM, wherein M is a photographically inactive cation or a metyl or ethyl group. Use of such compositions results in more efficient coupler usage and color products having yellow dyes with improved aging characteristics. The invention encompasses such liquid developer compositions, blends of (a) and (b), and the yellow dye-forming couplers, per se.

7 Claims, No Drawings

COLOR DEVELOPER COMPOSITIONS CONTAINING IMPROVED YELLOW DYE-FORMING COUPLER

This application is a continuation-in-part application of U.S. Ser. No. 449,880, filed Mar. 8, 1974, now abandoned and a division of application Ser. No. 492,116, filed July 26, 1974, now Pat. 3,929,484. This invention relates to diffusible yellow-dye-forming coupler compounds exhibiting good solubility properties, unusually high color-forming efficiency and, in the dye form, unusually good aging and absorption characteristics. Also, the present invention relates to developer compositions containing such valuable diffusible yellow-dye-forming coupler materials.

The coupler compounds of this invention are haloanilidophenoxycarboxy compounds having the structure I:

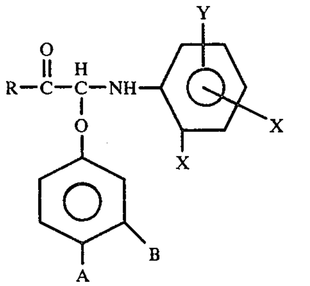

(I)

wherein R is a branched alkyl group containing 3 to 6 carbon atoms; X is Cl or Br; Y is X, hydrogen or alkyl (1 to 8 carbon atoms); and A and B differ and are either H or —COOM, wherein M is a photographically inactive cation, a methyl group or an ethyl group. This invention also includes developer compositions containing one or more of the compounds of the structure I and one or more organic aromatic amino developing agents, which developer compositions are used in the form of aqueous solutions comprising water and having a pH of at least about 10.

The formation of colored photographic images in silver halide emulsion layers by coupling the oxidation products of aromatic amino developing agents with color-forming coupler compounds is well known. Color-forming coupler compounds have been classified as "incorporated" and "diffusible," based upon the way such compounds are ordinarily used. For example, "incorporated" couplers have fairly large molecules in order to prevent the diffusion or substantial movement of such couplers within the particular hydrophilic colloid layer into which they were incorporated during the manufacture of the photographic element. By comparison, "diffusible" couplers are soluble in alkaline solutions which also usually contain one or more organic aromatic amino developing agents. Thus, when diffusible couplers are used, their capability of diffusing into (and through) the emulsion layers of the photographic element being treated makes it possible for them to react (couple) with oxidized aromatic amino color developer(s) and thereby become effectively bound into the emulsion layer. In this situation, unreacted diffusible coupler can be readily removed from the photographic element via simply washing the element with water.

Although many very useful diffusible couplers have been manufactured and used commercially heretofore, manufacturers of developer compositions are continually striving to discover couples having outstanding solubility, coupling efficiency and hydrolytic stability in developer compositions and excellent aging characteristics after they have been converted into the corresponding dyes during the color developing process.

Diffusible couplers that form yellow dyes have, to date, exhibited more of a need in this respect than have other types of color-forming couplers.

DESCRIPTION OF THE INVENTION

It has now been discovered that a small group or class of pivalyl αaryloxy anilide, yelloe-dye-forming coupler compounds displays the valuable characteristics set out above.

The valuable properties of the couplers (and compositions containing them) of the present invention apparently result from the unique combination of substituents on the basic ketomethylene backbone structure of the coupler compounds encompassed by Formula I above. Thus, it was known heretofore, as disclosed in U.S. Pat. Nos. 3,265,506 (now Reissue No. 27,848) and 3,408,194, that very good yellow dye stability and anti-stain properties result when couplers having (a) an aryloxy "coupling off" group attached through the ether linkage directly to the active carbon atom of the coupler and (b) a branched alkyl group (such as R in structure I above) attached to one of the activating carbonyl groups in an acetanilide coupler.

It has now been discovered that a still better coupler can result when c. there are two halogen substituents on the aromatic ring of the anilide portion of structure I, provided that one of the halogens is attached at the 2 position on the aromatic ring and that the halogens are identical; and d. there is a carboxyl substituent (either a carboxylic acid or a photographically inactive salt or lower alkyl ester thereof) attached at either the 3 or 4 position on the aromatic ring of the "aryloxy" coupling-off group. Preferred halogens, as in part (c) of the above disclosure, are Cl and Br. Of these, Cl is still further preferred. Similarly, it is preferred that a halogen be at both the 2 and 4 position on the aromatic ring of the acetanilide portion of structure I. Regarding the photographically inactive cation designated M in structure I, above, it is preferred that M be selected from the group consisting of H, alkali metal and ammonium cations and tertiary amines. Of those couplers having the structure I, particularly preferred in the practice of the present invention is alpha-pivalyl-alpha-(4-carboxyphenoxy)-2,4-dichloroacetanilide.

Hydrolytic Stability Test

As it was stated above, one of the valuable properties of the materials of the present invention relates to their surprisingly high resistance to hydrolysis under conditions which simulate end-use conditions; namely, in aqueous solution at a buffered pH of 12.06 and at a temperature of 23.9° C. Under such conditions, with the coupler being dissolved in the aqueous buffered solution at a concentration of coupler about $6.6 \times 10^{-5}$ molar, many couplers have been found to degrade (hydrolyze) at varying rates of hydrolysis. The rates of hydrolysis are apparently unaffected by the presence or absence of color developing agent in the solution. By monitoring the rate of disappearance of the coupler from the buffered solution (by measuring the solution absorption at the optimum wavelength at which the particular coupler anion absorbs), it was found that, generally, hydrolysis proceeded in a linear fashion, when the log of the absorption was plotted vs. time. As a result, relative rates of hydrolysis of couplers can be set out in terms of their respective "half-lives" in this standard test. In terms of hours, practical acceptability for very high quality diffusible couplers is believed to require half-lives of at least about 1000 hours. The half-lives of all of the coupler materials of the present invention are believed to substantially greater than 1000 hours in this test. (This has been confirmed by tests on some of the coupler compounds of structure I above.)

In order to demonstrate the excellent hydrolytic stability that can result from coupler compounds having the structure I, a number of coupler materials were submitted to the "hydrolytic stability" test described above. Results from that test are set out in Table I.

Table I

HYDROLYTIC STABILITY DATA
(Test at pH ≃ 12 and at T = 23.9° C.)

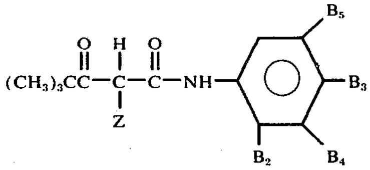

Structure II

| Coupler No. | Z | $B_2$ | $B_3$ | $B_4$ | $B_5$ | Half-life (hrs.) |
|---|---|---|---|---|---|---|
| 1 | Cl | $-OCH_3$ | H | H | H | 0.026 |
| 2 | 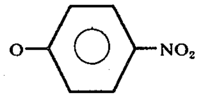 | $-OCH_3$ | H | H | H | 233 |
| 3 | 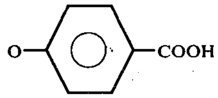 | $-OCH_3$ | H | H | H | 1132 |
| 4 | 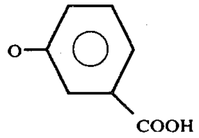 | $-OCH_3$ | H | H | H | 1430 |
| 5 | Cl | H | $-OCH_3$ | H | H | 0.012 |
| 6 | 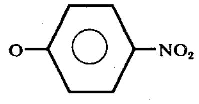 | H | $-OCH_3$ | H | H | 8 |
| 7 | Cl | Cl | H | H | H | 0.082 |
| 8 | 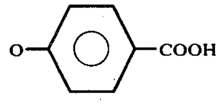 | Cl | H | H | H | 2180 |
| 9 | 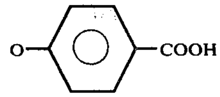 | Cl | Cl | H | H | >2500 |
| 10 | acetoxy | H | H | H | H | 0.01 |

It is expected that the presence of another substituent (such as alkoxy, halogen or alkyl) on the aromatic ring of the acetanilide portion of the couplers of this invention would not have an appreciable detrimental effect upon the hydrolytic stability of the resulting couplers as compared to that of the couplers which were involved in this test.

It is also noteworthy that the coupler compounds of the present invention exhibit a very high degree of color-forming efficiency. In view thereof, they can be used at somewhat lower concentrations in photographic processes if desired, in order to obtain yellow dye levels comparable to those presently obtainable by conventional methods using present commercial processes and coupler/color developer compositions. Alternatively, colored photographic materials having greater yellow dye density may be obtained via the practice of this invention, particularly when the invention is practiced commercially, using aqueous solutions of coupler, color developer and alkaline materials in the usual manipulative manner.

The compositions of the present invention comprise one or more p-phenylenediamine type color developing agents. Such agents are well known and need not be described in detail herein, since any phenylenediamine color developing agent can be used. A preferred p-phenylenediamine-type color developing agent is 4-amino-N-ethyl-N-(2-methoxyethyl)-m-toluidine, di-p-toluene-sulfonate salt. The coupler compounds of structure I can be used successfully in combination with such color developing agents. The ratio of color developing agent to coupler in the compositions of this invention can vary widely, but will generally be within the (molar) range of from about 0.2 to 1 to about 10 to 1, respectively, and preferably within the (molar basis) range of from about 0.5 to 1 to about 3 to 1. The coupler/color developer compositions of this invention are preferably blends of solid crystalline or powdered materials which blends can readily be dissolved in aqueous compositions in the preparation of color developer baths. Such baths, which contain yellow dye-forming coupler dissolved therein, can then be used in the conventional manner during the "yellow developer" step in a multi-stop process for manufacturing colored photographic articles. Use of the coupler compositions of this invention is demonstrated below in the Example.

The couplers of this invention can readily be manufactured via well known techniques, as set out in U.S. 3,408,194, for example, by simply using the appropriate raw materials.

In the following Example, all parts are by weight unless otherwise specified.

EXAMPLE

A conventional photographic element comprising a transparent poly(ethyleneterephthalate) support coated with a gelatin/Lippman emulsion (coating 910 mg silver/$m^2$) was exposed conventionally to a step scale of increasingly intense light. The exposed element was then subjected to the following developing procedure: (23.8° C)

| Step No. | Time | Accomplished |
|---|---|---|
| 1 | 5 minutes | Color Develop[1] |
| 2 | 5 minutes | Wash |
| 3 | 5 minutes | Fix[2] |
| 4 | 5 minutes | Wash |
| 5 | 5 minutes | Bleach[3] |
| 6 | 5 minutes | Wash |
| 7 | 5 minutes | Fix[2] |

-continued

| Step No. | Time | Accomplished |
|---|---|---|
| 8 | 10 minutes | Wash |

| | | |
|---|---|---|
| [1] Color Developer | | |
| soluble coupler (5 × $10^{-3}$ moles) | | |
| N,N-diethyl-p-phenylenediamine . HCl | 3.0 | g/l. |
| potassium bromide | 1.0 | g/l. |
| sodium sulfite | 0.65 | g/l. |
| potassium triphosphate | 15.0 | g/l. |
| pH adjusted to 12.0 at 23.8° C. | | |
| [2] Liquid Fix | | |
| sodium thiosulfate | 220 | g/l. |
| sodium sulfite | 10.0 | g/l. |
| sodium hydroxide | 0.15 | g/l. |
| [3] Bleach | | |
| sodium bromide | 35.0 | g/l. |
| potassium ferricyanide · 10 $H_2O$ | 200 | g/l. |
| sodium hydroxide | 0.1 | g/l. |
| sodium tetraborate . 5 $H_2O$ | 1.0 | g/l. |

Data resulting from subjecting the processed film strips to spectrophotometric absorption tests were recorded. In the following Tables II and III, "Dmax" values for several diffusable yellow-dye-forming couplers resulting from this type of test are shown. Couplers providing data for Table II were so-called "four-equivalent" couplers, while those providing data for Table III were "two-equivalent" couplers. Substituent groups appearing at the column headings in these Tables refer to the structural formula at the beginning of each table.

Table II

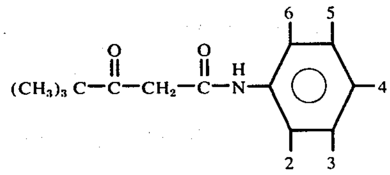

| Coupler No. | 2 | 3 | 4 | 5 | 6 | Dmax |
|---|---|---|---|---|---|---|
| 11 | F | H | F | H | H | 1.93 |
| 12 | Cl | Cl | H | H | H | 2.42 |
| 13 | Cl | H | Cl | H | H | 2.63 |
| 14 | Cl | H | H | Cl | H | 2.73 |
| 15 | H | Cl | Cl | H | H | 2.02 |
| 16 | Cl | H | H | H | Cl | 0.32 |
| 17 | Cl | H | Cl | $-NO_2$ | H | 1.98 |
| 18 | Cl | H | Cl | $-NH_2$ | H | 1.80 |
| 19 | Cl | H | Cl | $-NHSO_2CH_3$ | H | 1.03 |
| 20 | Cl | H | Cl | $-NHSO_2-pH-CH_3$ | H | 2.15 |
| 21 | Cl | H | $-NO_2$ | Cl | H | 2.10 |
| 22 | Cl | H | H | $-NHSO_2CH_3$ | H | 0.40 |
| 23 | Cl | H | H | $-CF_3$ | H | 2.60 |

Table III

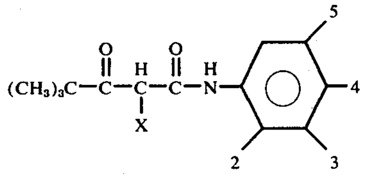

| Coupler No. | 2 | 3 | 4 | 5 | X | Dmax |
|---|---|---|---|---|---|---|
| 24 | $-OCH_3$ | H | H | H | —O—Ph—COOH—(p)— | 1.47 |
| 25 | Cl | H | H | H | —OCO—Ph | 1.52 |

Table III-continued
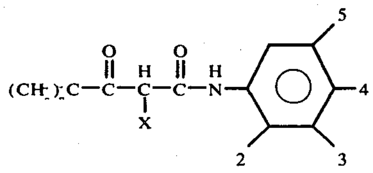
| Coupler No. | 2 | 3 | 4 | 5 | X | Dmax |
|---|---|---|---|---|---|---|
| 26 | Cl | H | H | H | 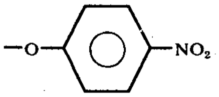 | 1.86 |
| 27 | Cl | H | H | H | 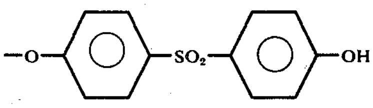 | 2.90 |
| 28 | Cl | H | H | H | 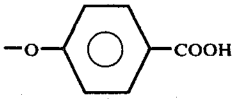 | 2.82 |
| 29 | H | H | H | H | 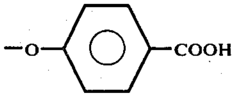 | 2.85 |
| 30 | Cl | Cl | H | H | 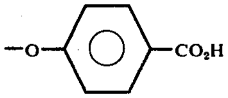 | 3.28 |
| 31 | Cl | H | Cl | H | 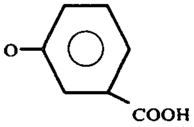 | 3.30 |
| 32 | Cl | H | Cl | H | 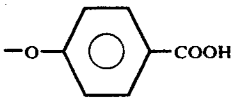 | 3.26 |
| 33 | Cl | H | H | Cl | 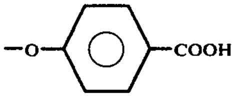 | 3.42 |
| 34 | Cl | H | Cl | Cl | 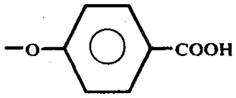 | 3.8 |
| 35 | Cl | H | Cl | Cl | 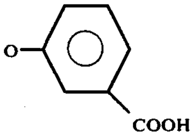 | 3.32 |

Illustrative Manufacture of Coupler Material

Step 1

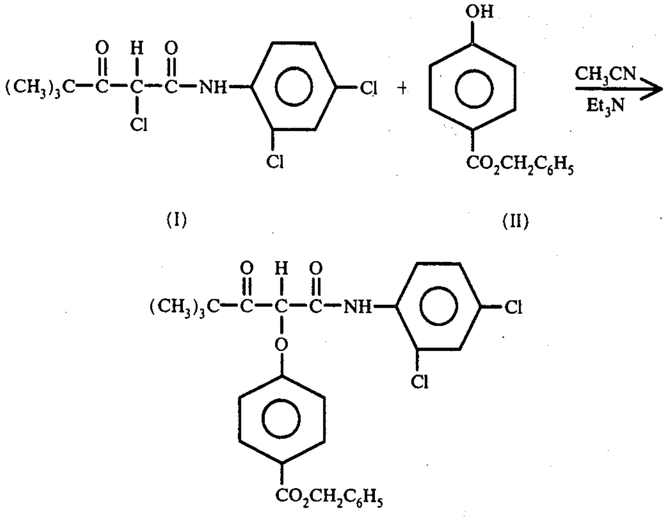

(I) (II)

(III)

A solution of 76.9 g of the amide (I) and phenol (II) in 400 ml of acetonitrile containing 30.1 g. triethylamine was heated at reflux for 2½ hours. The solution was then evaporated in vacuum. The resulting solid material was dissolved in 500 ml chloroform, extracted 3 times with 100 ml water and then dried over $M_gSO_4$, filtered, and concentrated in vacuum. The resulting yellow syrup as dissolved in 200 ml methanol and crystallized at room temperature. The dried crystalline product had a melting point of 92°–95° C.

Step 2

(Product from Step 1)
(III)

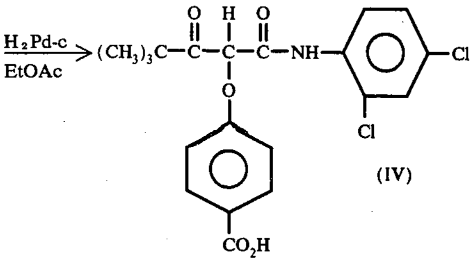

(IV)

A solution of 51.4 g of the product from Step 1, above, in 300 ml ethyl acetate and 2.0 g of 10% palladium on carbon was shaken under 40 psi of hydrogen until hydrogen uptake ceased. Then the solution was warmed to completely dissolve the product. The resulting suspension was filtered to remove catalyst, and the filtrate was dried. The pale, pink solid material was recrystallized twice with methanol containing charcoal (for color improvement) to yeild a product (Compound IV) having a melting point of 185°–187.5° C.

The invention has been described in detail with particular reference to preferred embodiments thereof, but, it will be understood that variations and modifications can be effected within the spirit and scope of the invention.

What is claimed is:

1. A coupler compound capable of reacting with oxidized aromatic amino color developer agent to form a yellow dye, said compound having the structure:

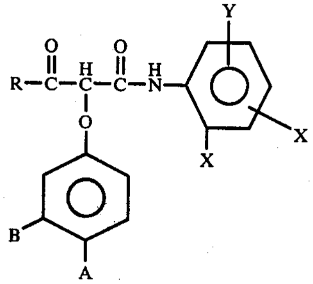

wherein R is a branched alkyl group containing 3 to 6 carbon atoms; X is Cl or Br; Y and X, hydrogen or alkyl (1 to 8 carbon atoms); and A and B differ and are either H or —COOM, wherein M is a photographically inactive cation or a methyl or ethyl group.

2. A coupler compound capable of reacting with oxidized aromatic amino color developer agent to form a yellow dye, said compound having the structure:

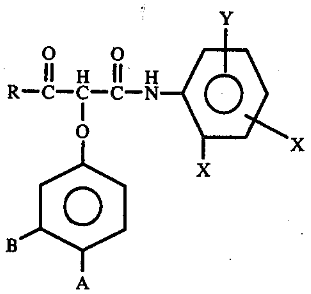

wherein R is a branched alkyl group containing 3 to 6 carbon atoms; X is Cl; Y is H; and A and B differ and are either H or —COOM, wherein M is H, alkali metal or ammonium.

3. α-4-carboxyphenoxy-α-pivalyl-2,4-dichloroacetanilide.

4. α-3-carboxyphenoxy-α-pivalyl-2,4-dichloroacetanilide.

5. α-4-carboxyphenoxy-α-pivalyl-2,3-dichloroacetanilide.

6. α-3-carboxyphenoxy-α-pivalyl-2,4,5-trichloroacetanilide.

7. α-4-carboxyphenoxy-α-pivalyl-2,5-dichloroacetanilide.

* * * * *

UNITED STATES PATENT AND TRADEMARK OFFICE

CERTIFICATE OF CORRECTION

PATENT NO. : 3,994,967

DATED : November 30, 1976

INVENTOR(S) : Robert E. Ross

It is certified that error appears in the above-identified patent and that said Letters Patent are hereby corrected as shown below:

Column 10, line 52, "Y and X" should read ---Y is X---.

Signed and Sealed this

Twenty-sixth Day of April 1977

[SEAL]

*Attest:*

RUTH C. MASON
*Attesting Officer*

C. MARSHALL DANN
*Commissioner of Patents and Trademarks*